United States Patent [19]

Niesor et al.

[11] Patent Number: 6,127,350
[45] Date of Patent: Oct. 3, 2000

[54] USE OF PHENOL SUBSTITUTED DIPHOSPHONATES AS ANTINEOPLASTIC AGENTS

[75] Inventors: Eric Niesor, Nyon; Craig Leigh Bentzen, Bogis-Boseey; Lan Mong Nguyen, Nyon; Jean-Luc Thuillard, Saint-Cergue; Hieu Trung Phan, Tannay; Jean Flach, Lausanne, all of Switzerland

[73] Assignee: Symphar S.A., Versoix, Sweden

[21] Appl. No.: 09/011,247

[22] PCT Filed: Jul. 26, 1996

[86] PCT No.: PCT/EP96/03301

§ 371 Date: Jan. 28, 1998

§ 102(e) Date: Jan. 28, 1998

[87] PCT Pub. No.: WO97/04785

PCT Pub. Date: Feb. 13, 1997

[30] Foreign Application Priority Data

Jul. 28, 1995 [CH] Switzerland .............................. 2213/95

[51] Int. Cl.[7] ................................................... A01N 57/00
[52] U.S. Cl. ............................................................... 514/107
[58] Field of Search ............................................... 514/107

[56] References Cited

U.S. PATENT DOCUMENTS 5,043,330  8/1991  Nguygen et al. .......................... 514/107
5,128,331  7/1992  Nguygen et al. .......................... 514/101

FOREIGN PATENT DOCUMENTS

0339237A2  of 1989  European Pat. Off. .
0440809A1  of 1991  European Pat. Off. .

OTHER PUBLICATIONS

"Gene–based Therapy", The Year's Drug News, 459–462, 1994.

Bolton et al., "Ras Oncogene Directed Approaches in Cancer Chemotherapy", Annual Reports in Medicinal Chemistry–29, 17, 165–174, 1994.

*Primary Examiner*—Jerome D. Goldberg
*Attorney, Agent, or Firm*—Heslin & Rothenberg, P.C.

[57] ABSTRACT

A method of treating or preventing neoplastic disease and a method of preventing transformation of a normal cell into a tumor cell by mutated ras activities, utilizing a compound of formula I are disclose.

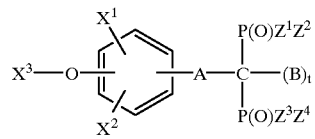

16 Claims, No Drawings

USE OF PHENOL SUBSTITUTED DIPHOSPHONATES AS ANTINEOPLASTIC AGENTS

The present invention relates to antineoplastic agents, and in particular to the use of phenol substituted gem-diphosphonate derivatives in the treatment of neoplastic diseases. More specifically, the present invention provides the use of certain phenol substituted gem-diphosphonate derivatives for the preparation of pharmaceutical compositions useful in the treatment and prevention of cancers and metastasis and in particular useful in the treatment and prevention of ras oncogene dependent cancers and metastatic invasions.

The majority of existing anticancer drugs are cytotoxic compounds which lack specificity for killing tumor cells and therefore also affect normal cells, resulting in toxic side effects. There remains therefore a need for the development of more specific agents acting on the cell signalling pathways leading to the inhibition of cancer cell proliferation without affecting normal cell proliferation (Oncolytic Drugs, J. R. Prous, The Year's Drug News, 1994 edition, p.459 and Ras Oncogene Directed Approaches in Cancer Chemotherapy, G. Bolton et. al., Annual Reports in Medicinal Chemistry 1994; 29: 165–174).

Mutations of the ras oncogene have been shown to be present in a wide variety of human tumors and may contribute to as many as one-fifth of all human cancers. Specifically, it is found in more than fifty percent of colon and ninety percent of pancreatic carcinomas. Ras mutations are therefore considered to play a key role in triggering cancer formation and development (J. L. Bos, Cancer Res. 1989;49:4682–4689). It has also been established that the mutated forms of ras protein are present only in tumors and not in normal tissues of cancer patients. Blocking the activity of ras mutations to transform normal cells into cancer cells as well as to further promote the development of cancer cells and tumors is therefore an attractive therapeutic target.

The U.S. Pat. No. 5,043,330 (1991) corresponding to the European Patent No. 0,339,237 discloses the synthesis of a class of phenol substituted gem-diphosphonate derivatives and their utility as lipid lowering agents, for example in the treatment of cardiovascular diseases.

The present applicants have now found that diphosphonates of the type disclosed in U.S. Pat. No. 5,043,330 are surprisingly effective for inhibiting specifically the proliferation as well as inducing apoptosis in cancer cells without being cytotoxic to normal cells.

Accordingly, in one aspect, the invention provides the use of a compound for the manufacture of a medicament for the treatment of neoplastic diseases, said compound having the following formula (I):

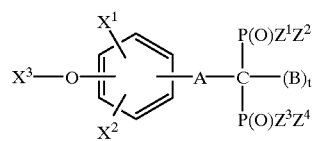

(I)

where:
$Z^1$, $Z^2$, $Z^3$ and $Z^4$ are identical or different and are
  OR where R is H, a straight, branched or cyclic alkyl group comprising from 1 to 8 carbon atoms,
  OM where M is a cation,
  $NR_2$ where R has the same meaning as defined above,
  $Z^1$, $Z^2$ and $Z^3$, $Z^4$ may form an alkylidenedioxy ring comprising 2 to 8 carbon atoms,
$X^1$ and $X^2$ are identical or different and are H, a halogen atom, a straight, branched or cyclic alkyl or alkoxy group from 1 to 8 carbon atoms,
$X^3$ is H, an alkyl group $R^1$ from 1 to 4 carbon atoms, an acyl group $C(O)R^1$, a carbamyl group $C(O)NHR^1$ where $R^1$ is described as above, $X^3O$ and one of the two other substituents $X^1$ or $X^2$ may form an alkylidenedioxy ring comprising from 1 to 4 carbon atoms,
A is $—CH=CH—CH_2—$, $—(CH_2)_n—$, $—O(CH_2)_n—$, $—S—$, $—SO_2—$, $—S(CH_2)_n—$, $—SO_2(CH_2)_n—$, where n is an integer from 1 to 7, or together with B forms an alkylidene group of the formula $(CH=CH)_k—(CH_2)_d—CH=$ where k is zero or 1 and d is an integer from zero to 4,
B is H, an alkyl group from 1 to 4 carbon atoms,
t is zero or 1, with the proviso that t is zero only when A is $(CH=CH)_k—(CH_2)_d—CH=$ where k and d are as described above.

The compounds of formula (I) can exist as salts and references to the compounds of formula (I) hereinafter include the salt forms of the compounds, unless the context indicates otherwise. Examples of salts are compounds of formula (I) wherein one or more of the groups $Z^1$, $Z^2$, $Z^3$ and $Z^4$ are constituted by the group OM where M is an alkaline or alkaline earth metal ion or an ammonium group $NR_4$ where R has the same meaning as defined above.

In another aspect the invention provides the use of a compound of the formula (I) as hereinbefore defined for the manufacture of a medicament for treating solid tumors, for example colon, pancreas, thyroid, lung, breast, head and neck tumors.

In another aspect the invention provides the use of a compound of the formula (I) as hereinbefore defined for the manufacture of a medicament for treating tumors of the hemopoietic and immune system, for example lymphomas and leukemias.

In still another aspect the invention provides the use of a compound of the formula (I) as hereinbefore defined for the manufacture of a medicament for treating patients with metastasis of primary tumors.

In a further aspect, the invention provides the use of a compound of formula (I) as hereinbefore defined for the manufacture of a medicament for preventing the transformation of normal cells or inhibiting metastatic invasion of normal tissues by cancer cells.

In a still further aspect, the invention provides a method of treatment of neoplastic diseases or prevention of cancer metastasis, and in particular ras-dependent cancers, which method comprises administering to a patient suffering from said cancer or the potential of cancer development, an effective therapeutic amount of a compound of the formula (I) as hereinbefore defined.

The invention also includes within its scope a method for selectively eradicating cancer cells which comprises treating a mixture of cancer cells and normal cells from a patient in an ex vivo manner with a compound of the formula (I), further to which the cells are reintroduced into the patient. Thus, for example, in accordance with this method, blood, plasma or other fluids can be drawn off from the patient, treated with the compounds of formula (I) ex vivo, and then reintroduced into the patient.

In the compounds of formula (I), examples of groups $Z^1$, $Z^2$, $Z^3$ and $Z^4$ include hydroxy, methoxy, ethoxy, n-propyloxy, isopropyloxy, n-butyloxy, sec-butyloxy and tert-butyloxy. A preferred group is the isopropyloxy group.

It is presently preferred that the groups $Z^1$, $Z^2$, $Z^3$ and $Z^4$ are identical and in a particularly preferred embodiment of the invention $Z^1$, $Z^2$, $Z^3$ and $Z^4$ are all isopropyloxy.

Examples of groups $X^1$ and $X^2$ include hydrogen, straight or branched alkyl groups and alkoxy groups having from 1 to 5 carbon atoms, more particularly from 1 to 4 carbon atoms. Preferred groups $X^1$ and $X^2$ are methyl, ethyl, n-propyl, isopropyl, sec-butyl, tert-butyl, methoxy and ethoxy groups, a particularly preferred group being tert-butyl.

Examples of groups $X^3$ include hydrogen, $C_{1-4}$ alkyl and $C_{1-4}$ alkanoyl, hydrogen being particularly preferred at present.

The compounds of formula (I) include the phenol substituted alkylidenediphosphonates (Ia) and the phenol substituted alkenylidenediphosphonates (Ib).

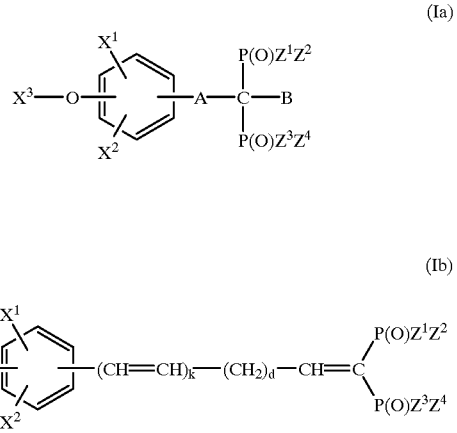

where
$X^1$, $X^2$, $X^3$, A, B, k, d, $Z^1$, $Z^2$, $Z^3$ and $Z^4$ are as described above.

Compounds of structure (Ia) include, for example, those in which:
$X^1$ and $X^2$ are identical or different and are alkyl groups from 1 to 8 carbon atoms,
$X^3$ is hydrogen,
A is CH=CH—$CH_2$, $(CH_2)_n$, S, $SO_2$, S—$(CH_2)_n$, $SO_2$—$(CH_2)_n$, where n is 1–7,
B is hydrogen or a $C_1$–$C_4$ alkyl group,
$Z^1$, $Z^2$, $Z^3$ and $Z^4$ are identical or different and are OH, alkoxy groups of 1 to 8 carbon atoms or one or both of the pairs $Z^1$, $Z^2$ and $Z^3$, $Z^4$ are an alkylidenedioxy group of 2 to 8 carbon atoms.

Compounds of structure (Ib) include, for example, those in which
$X^1$ and $X^2$ are identical or different and are alkyl groups from 1 to 8 carbon atoms,
$X^3$ is hydrogen,
k is zero or 1 and d is zero to 4,
$Z^1$, $Z^2$, $Z^3$, $Z^4$ identical or different are OH, alkoxy groups of 1 to 8 carbon atoms or one or both of the pairs $Z^1$, $Z^2$ and $Z^3$, $Z^4$ are an alkylidenedioxy group of 2 to 8 carbon atoms.

Particular examples of compounds of formula (I) for use in the present invention include the compounds in Tables 1 a and 1 b.

This invention provides a new use of gem-diphosphonates of formula (I) for the treatment of neoplastic diseases and prevention of cancers and metastasis, and more particularly those which are ras dependent. In a particular preferred embodiment, it provides a new use of Compound 1 of formula (I), wherein $X^1$ and $X^2$ are both tert-butyl respectively at the 3- and 5- positions, $X^3$ is H at the 4-position, A is $CH_2$, B is H, t is 1 and $Z^1$, $Z^2$, $Z^3$, $Z^4$ all are iso-propyloxy for the preparation of pharmaceutical compositions useful for the treatment of cancers. Said Compound 1 has the following structure, formula and physicochemical properties:

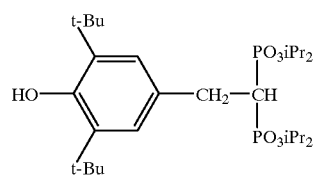

Tetraisopropyl 2-(3,5-di-tert-butyl4-hydroxyphenyl)-ethylidene-1,1-diphosphonate, $C_{28}H_{52}O_7P_2$, mp=104–105° C.

The compounds of the invention can be prepared according to the methods described in EP 0 339 237 A, the disclosure of which is incorporated by reference herein, or by methods analogous thereto.

Some of the analogs are novel. Accordingly, in a further aspect, the invention provides a novel compound selected from:
tetraisopropyl 2-(3, 5-diisopropyl-4-hydroxyphenyl)-ethenylidene-1,1-diphosphonate,
tetraisopropyl 2-(3,5-diisopropyl-4-hydroxyphenyl)-ethylidene-1,1-diphosphonate,
tetraisopropyl 2-(3,4,5-trimethoxyphenyl )-ethenyl idene-1, 1-diphosphonate,
tetraisopropyl 2-(3,4,5-trimethoxyphenyl)-ethylidene-1,1-diphosphonate,
tetraisopropyl 2-(3-tert-butyl4-hydroxy-5-methylphenyl)-ethenylidene-1,1 -diphosphonate,
tetraisopropyl 2-(3-tert-butyl-4-hydroxy-5-methylphenyl)-ethylidene-1,1-diphosphonate,
tetraisopropyl 2-(3-ethoxy4-hydroxyphenyl)-ethenylidene-1,1-diphosphonate,
tetraisopropyl 2-(3-ethoxy-4-hydroxyphenyl)-ethylidene-1, 1-diphosphonate,
tetraethyl 2-(3,5-di-tert-butyl-4-methoxyphenyl)-ethenylidene-1,1-diphosphonate and
tetraisopropyl 1-(3,5-di-tert-butyl-4-hydroxyphenyl) butylidene-2,2-diphosphonate.

The compounds of formula (I) can be administered orally, or by delivery across another mucosal surface (for example across the nasal, buccal, bronchial or rectal mucosa), transdermally, or by injection (for example intradermal, intraperitoneal, intravenous or intramuscular injection).

When the compounds are intended for oral administration, they can be formulated, for example, as tablets, capsules, granules, pills, dragees, lozenges, powders, solutions, emulsions, syrups, suspensions, or any other pharmaceutical form suitable for oral administration. Oral dosage forms can, if desired, be coated with one or more release delaying coatings to allow the release of the active compound to be controlled or targeted at a particular part of the enteric tract.

Tablets and other solid or liquid oral dosage forms can be prepared in standard fashion from the compounds of formula (I) and a pharmaceutically acceptable solubilizer, diluent or carrier. Examples of solubilizers, diluents or carriers include sugars such as lactose, starches, cellulose and its derivatives, powdered tracaganth, malt, gelatin, talc, stearic acid, magnesium stearate, calcium sulfate, vegetable oils, polyols such as glycerol, propyleneglycol and polyethyleneglycols, alginic acids and alginates, agar, pyrogen free water, isotonic saline, phosphate buffered solutions, and optionally other pharmaceutical excipients such as disintegrants, lubricants, wetting agents such as sodium lauryl sulfate, coloring agents, flavoring agents and preservatives, etc.

Capsules can be of the hard or soft variety and can contain the active compound in solid, liquid or semisolid form. Typically such capsules are formed from gelatine or an equivalent substance and can be coated or uncoated. If it is desired to delay the release of the active compound until the capsule has passed through the stomach and into the intestine, the capsule can be provided with a pH sensitive coating adapted to dissolve at the pH found in the duodenum or ileum. Examples of such coatings include the Eudragits, the uses of which are well known.

Formulations for injection will usually be made up of the appropriate solubilizers such as detergents which may also include compounds and excipients such as buffering agents to provide an isotonic solution having the correct physiological pH. The injectable solutions are typically pyrogen-free and can be provided in sealed vials or ampoules containing a unit dose of compound.

A unit dosage form of the compounds of the invention typically will contain from 0.1% to 99% by weight of the active substance, more usually from 5% to 75% of the active substance. By way of example, a unit dosage form can contain from 1 mg to 1 g of the compound, more usually from 10 mg to 500 mg, for example between 50 mg and 400 mg, and typically in doses of 100 mg to 200 mg.

The compounds of the invention will be administered in amounts which are effective to provide the desired therapeutic effect. The concentrations necessary to provide the desired therapeutic effect will vary according to among other things the precise nature of the disease, the size, weight and age of the patient and the severity of the disease.

The doses administered will preferably be non-toxic to the patient, although in certain circumstances the severity of the disease under treatment may necessitate administering an amount of compound which causes some signs of toxicity.

Typically, the compounds of the invention will be administered in amounts in the range 0.01 mg/kg to 100 mg/kg bodyweight, more preferably 0.1 mg/kg to 10 mg/kg bodyweight and particularly 1 mg/kg to 5 mg/kg bodyweight. For an average human of 70 kg weight, a typical daily dosage of the compounds of the invention would be in the range of 70 mg to 700 mg. Such a dosage can be administered, for example from two to four times daily. Ultimately however, the size of the doses administered and the frequency of administration will be at the discretion and judgement of the physician treating the patient.

Example K is provided to illustrate a representative batch formula used by the applicants to prepare capsules of Compound 1.

The pharmacological activity of the compounds of the present invention can be demonstrated by means of an in vitro screening model using a clone of NIH 3T3 cells transfected with the human bladder cancer T24 (H-ras) oncogene. This cell line (PAP2) has been selected based upon its characterisation of a high level of ras expression and ras-dependent activities which correlate with the high level of metastatic ability (S. A. Hill et al., in J. of the National Cancer Institute 1988; 80: 484–490 and A. Chambers et. al. in Invasion and Metastasis 1990; 10: 225–240). The PAP2 cell line has been shown to have a ras-dependent increased expression of cathepsins, cysteine proteinases implicated in the processes of metastasis (A. Chambers et al., in Molecular Carcinogenesis 1992; 5:238–245). Thus PAP2 cells exhibit functions which are relevant to the pathogenesis of human cancers. These cells were used for testing in vitro the effect of compounds on cell proliferation, proteolytic enzyme activity (metastasis) and apoptosis (programmed cell death). When injected s.c. in immunodeficient (nude) mice these cells rapidly form solid tumours and the anticancer activity of the tested compounds were measured in vivo after oral administration.

The results of a series of in vitro and in vivo tests led to the discovery by the applicants that representative compounds of formula (I) and in particular Compound 1,
inhibit the growth of cancer cells in tissue culture,
induce apoptosis in cancer cells in tissue culture,
inhibit proteases in cancer cells which are involved in metastasis, and
demonstrate anti-cancer activity in nude mice bearing solid tumors. The experimental results presented in Tables 1–7b provide evidence that compounds of formula (I), and in particular Compound 1, are potentially useful in the treatment of neoplastic diseases which include cancers of the hemopoietic and immune system, such as lymphomas and leukemias, as well as cancers of the pancreas, colon, breast, thyroid, brain, lung, head and neck. This recently discovered anticancer activity of compounds of formula (I) is unexpected and is independent of their previously reported activities as lipid lowering agents.

Results are expressed as mean±sem. Significance of difference was estimated using the Student t-test for unpaired data.

EXAMPLE 1

INHIBITION OF RAS-DEPENDENT CELLULAR PROLIFERATION BY COMPOUNDS OF FORMULA (I)

A series of compounds of formula (I) were screened to determine the most active compounds and structure activity relationships. The inhibition of PAP2 cell proliferation was selected as an initial screening test.

Briefly, PAP2 cells were seeded at a concentration of $3 \times 10^4$ per well in 24-well plates and were allowed to attach for 24 h. Test compounds were added at 10 and 20 µM final concentrations in 1% ethanol solutions. Cells were trypsinized after 48 h incubation and viable cells (excluding Trypan blue) were counted. The results obtained are listed in Tables 1 a and 1 b for the series of Compounds (Ia) and (Ib) respectively.

The compounds screened in this test were synthesized according to the procedures described in the U.S. Pat. No. 5,043,330 (1991) corresponding to the European patent 0 339 237. Some examples (Examples A–J) are provided to further illustrate the synthesis of novel derivatives according to the procedures described in the above-mentioned prior art documents.

TABLE 1a

Effect of phenol substituted gem-diphosphonates (Ia) on PAP2 Cells (Ia)

$$X^3-O-\underset{X^2}{\overset{X^1}{\bigcirc}}-A-\underset{P(O)Z^3Z^4}{\overset{P(O)Z^1Z^2}{\underset{|}{C}}}-B$$

| Cpd | $X^1$ | $X^2$ | $X^3$ | A | B | $Z^1$ | $Z^2$ | $Z^3$ | $Z^4$ | Cell (% count control) 10 μM | 20 μM |
|---|---|---|---|---|---|---|---|---|---|---|---|
| 1 | 3-t-Bu | 5-t-Bu | 4-H | $CH_2$ | H | Oi-Pr | Oi-Pr | Oi-Pr | Oi-Pr | −70 | −100 |
| 2 | 3-t-Bu | 5-t-Bu | 4-H | $CH_2$ | H | OH | OH | OH | OH | −31 | −45 |
| 3 | 3-t-Bu | 5-t-Bu | 4-H | $CH_2$ | H | OMe | OMe | OMe | OMe | −21 | −17 |
| 4 | 3-t-Bu | 5-t-Bu | 4-H | $CH_2$ | H | OEt | OEt | OEt | OEt | −30 | −22 |
| 5 | 3-t-Bu | 5-t-Bu | 4-H | $CH_2$ | H | On-Pr | On-Pr | On-Pr | On-Pr | −22 | −89 |
| 6 | 3-t-Bu | 5-t-Bu | 4-H | $CH_2$ | H | On-Bu | On-Bu | On-Bu | On-Bu | −26 | −51 |
| 7 | 3-s-Bu | 5-s-Bu | 4-H | $CH_2$ | H | OEt | OEt | OEt | OEt | −6 | +3 |
| 8 | 3-s-Bu | 5-s-Bu | 4-H | $CH_2$ | H | Oi-Pr | Oi-Pr | Oi-Pr | Oi-Pr | −21 | −45 |
| 9 | 3-i-Pr | 5-i-Pr | 4-H | $CH_2$ | H | OEt | OEt | OEt | OEt | −16 | −31 |
| 10 | 3-i-Pr | 5-i-Pr | 4-H | $CH_2$ | H | Oi-Pr | Oi-Pr | Oi-Pr | Oi-Pr | −20 | −51 |
| 11 | 3-t-Bu | 5-Me | 4-H | $CH_2$ | H | OEt | OEt | OEt | OEt | −14 | −37 |
| 12 | 3-t-Bu | 5-Me | 4-H | $CH_2$ | H | Oi-Pr | Oi-Pr | Oi-Pr | Oi-Pr | −3 | −27 |
| 13 | 3-t-Bu | 5-t-Bu | 4-H | S | H | OEt | OEt | OEt | OEt | −19 | −39 |
| 14 | 3-t-Bu | 5-t-Bu | 4-H | S | H | Oi-Pr | Oi-Pr | Oi-Pr | Oi-Pr | −53 | −90 |
| 15 | 3-OMe | 5-OMe | 4-Me | $CH_2$ | H | Oi-Pr | Oi-Pr | Oi-Pr | Oi-Pr | −23 | −5 |
| 16 | 3-OEt | 5-H | 4-H | $CH_2$ | H | Oi-Pr | Oi-Pr | Oi-Pr | Oi-Pr | −2 | +5 |
| 17 | 3-t-Bu | 5-t-Bu | 4-H | $CH_2$ | H | OEt | OEt | On-Bu | On-Bu | −6 | −95 |
| 18 | 3-t-Bu | 5-t-Bu | 4-H | $CH_2$ | H | OEt | OEt | Oi-Pr | Oi-Pr | −46 | −59 |
| 19 | 3-t-Bu | 5-t-Bu | 4-H | $CH_2$ | Et | OEt | OEt | OEt | OEt | −21 | −36 |
| 20 | 6-Cl | 3,4-$OCH_2$ | | $CH_2$ | H | OEt | OEt | OEt | OEt | +20 | −9 |
| 21 | 3-t-Bu | 5-t-Bu | 4-H | $CH_2$ | H | $O(CH_2)_3O$ | | $O(CH_2)_3O$ | | −32 | −28 |
| 22 | 3-OMe | 5-OMe | 4-H | $CH_2$ | H | OEt | OEt | OEt | OEt | | |
| 23 | 3-OMe | 5-OMe | 4-H | $CH_2$ | H | Oi-Pr | Oi-Pr | Oi-Pr | Oi-Pr | | |
| 24 | 3-t-Bu | 5-t-Bu | 4-H | $CH_2$ | Et | Oi-Pr | Oi-Pr | Oi-Pr | Oi-Pr | −25 | −40 |

TABLE 1b

Effect of phenol substituted gem-diphosphonates (Ib) on PAP2 Cells (Ib)

$$X^3-O-\underset{X^2}{\overset{X^1}{\bigcirc}}-(CH=CH)_k-(CH_2)_d-CH=C\underset{P(O)Z^3Z^4}{\overset{P(O)Z^1Z^2}{}}$$

| Cpd | $X^1$ | $X^2$ | $X^3$ | k | d | $Z^1$ | $Z^2$ | $Z^3$ | $Z^4$ | Cell count (% control) 10 μM | 20 μM |
|---|---|---|---|---|---|---|---|---|---|---|---|
| 25 | 3-t-Bu | 5-t-Bu | 4-H | 0 | 0 | OH | OH | OH | OH | | |
| 26 | 3-t-Bu | 5-t-Bu | 4-H | 0 | 0 | OMe | OMe | OMe | OMe | −33 | −17 |
| 27 | 3-t-Bu | 5-t-Bu | 4-H | 0 | 0 | OEt | OEt | OEt | OEt | −48 | −45 |
| 28 | 3-t-Bu | 5-t-Bu | 4-H | 0 | 0 | Oi-Pr | Oi-Pr | Oi-Pr | Oi-Pr | −28 | −46 |
| 29 | 3-t-Bu | 5-t-Bu | 4-H | 0 | 0 | On-Pr | On-Pr | On-Pr | On-Pr | −51 | −63 |
| 30 | 3-t-Bu | 5-t-Bu | 4-H | 0 | 0 | On-Bu | On-Bu | On-Bu | On-Bu | −13 | −31 |
| 31 | 3-s-Bu | 5-s-Bu | 4-H | 0 | 0 | OEt | OEt | OEt | OEt | −30 | −44 |
| 32 | 3-s-Bu | 5-s-Bu | 4-H | 0 | 0 | Oi-Pr | Oi-Pr | Oi-Pr | Oi-Pr | −13 | −54 |
| 33 | 3-i-Pr | 5-i-Pr | 4-H | 0 | 0 | OEt | OEt | OEt | OEt | −5 | +13 |
| 34 | 3-i-Pr | 5-i-Pr | 4-H | 0 | 0 | Oi-Pr | Oi-Pr | Oi-Pr | Oi-Pr | −26 | −62 |
| 35 | 3-t-Bu | 5-Me | 4-H | 0 | 0 | OEt | OEt | OEt | OEt | −14 | −14 |
| 36 | 3-t-Bu | 5-Me | 4-H | 0 | 0 | Oi-Pr | Oi-Pr | Oi-Pr | Oi-Pr | −24 | −7 |
| 37 | 3-OMe | 5-OMe | 4-H | 0 | 0 | OEt | OEt | OEt | OEt | −3 | −28 |
| 38 | 3-OMe | 5-OMe | 4-H | 0 | 0 | Oi-Pr | Oi-Pr | Oi-Pr | Oi-Pr | | |
| 39 | 3-OMe | 5-OMe | 4-Me | 0 | 0 | Oi-Pr | Oi-Pr | Oi-Pr | Oi-Pr | −17 | −34 |

TABLE 1b-continued

Effect of phenol substituted gem-diphosphonates (Ib) on PAP2 Cells $$X^3-O-\underset{X^2}{\overset{X^1}{\diamondsuit}}-(CH=CH)_k-(CH_2)_d-CH=C\underset{P(O)Z^3Z^4}{\overset{P(O)Z^1Z^2}{<}} \quad (Ib)$$

| | | | | | | | | | Cell count (% control) | |
|---|---|---|---|---|---|---|---|---|---|---|
| Cpd | $X^1$ | $X^2$ | $X^3$ | k | d | $Z^1$ | $Z^2$ | $Z^3$ | $Z^4$ | 10 µM | 20 µM |
| 40 | 3-OEt | 5-H | 4-H | 0 | 0 | Oi-Pr | Oi-Pr | Oi-Pr | Oi-Pr | −30 | −23 |
| 41 | 3-t-Bu | 5-t-Bu | 4-H | 1 | 0 | OEt | OEt | OEt | OEt | −40 | −77 |
| 42 | 3-t-Bu | 5-t-Bu | 4-H | 1 | 0 | Oi-Pr | Oi-Pr | Oi-Pr | Oi-Pr | −36 | −71 |
| 43 | 3-t-Bu | 5-t-Bu | 4-H | 0 | 0 | OEt | OEt | On-Bu | On-Bu | −18 | −54 |
| 44 | 3-t-Bu | 5-t-Bu | 4-H | 0 | 0 | OEt | OEt | Oi-Pr | Oi-Pr | −17 | −28 |
| 45 | 3-t-Bu | 5-t-Bu | 4-Me | 0 | 0 | OEt | OEt | OEt | OEt | −10 | −33 |
| 46 | H | 3,4-OCH$_2$ | | 0 | 0 | OEt | OEt | OEt | OEt | −22 | −26 |
| 47 | H | 3,4-(OCH$_2$)$_2$ | | 0 | 0 | OEt | OEt | OEt | OEt | −11 | −30 |

EXAMPLE 2

In vitro Results

INHIBITION OF RAS-DEPENDENT CELLULAR PROLIFERATION

Cell culture

H-Ras-transfected NIH 3T3 cells (PAP2) (S. A. Hill et al.; J Natl. Cancer Inst. 1988;80:484–490) were grown at 37° C. in a 5% $CO_2$ atmosphere in Dulbecco's modified Eagle medium (DMEM) with 25 mM HEPES and 10% fetal calf serum. PAP2 cells were trypsinized and subcultured twice a week prior confluency.

1. Inhibition of Cell proliferation

The effects of Compound 1 on cellular proliferation were monitored by two methods:

cell count with a hemacytometer and concurrent DNA determination cell number estimation by calorimetric assay.

1.1. Cell count and DNA content

Briefly, PAP2 cells were seeded at a concentration of $3 \times 10^4$ per dish in 24-well plates 4 h before the addition of increasing concentrations of the tested compound. Cells were trypsinized at daily intervals. An aliquot of the cell suspension was counted with a hemacytometer. The remaining cells were lysed in 0.01N NaOH and DNA concentration was determined by spectrofluorimetry using 4,6-diamidino-2-phenylindole as fluorochrome and calf thymus DNA as standard.

TABLE 2a

Inhibition of the Proliferation of PAP2 Cells by Compound 1 (cell number/well)

| | Compound 1 concentration | | | | | |
|---|---|---|---|---|---|---|
| | 0 | 0.1 µM | 0.5 µM | 1.0 µM | 5.0 µM | 10 µM |
| Cell nb/well | 273750 | 256250 | 208750 | 186250 | 102500 | 71250 |
| sem | 9437 | 7465 | 4270 | 15861 | 5951 | 8260 |
| % change | | −6 | −24 | −32 | −63 | −74 |
| p | | 0.196 | 0.001 | 0003 | 0.001 | 0.001 |

The calculated IC50 value of Compound 1 for the inhibition of the growth of PAP2 cells is 1.02 µM.

TABLE 2b

Decrease in DNA Concentration Produced by Compound 1 in Cultured PAP2 Cells DNA (mg/well)

| | Compound 1 concentration | | | | | |
|---|---|---|---|---|---|---|
| | 0 | 0.1 µM | 0.5 µM | 1.0 µM | 5.0 µM | 10 µM |
| Cell nb/well | 4.62 | 4.40 | 4.04 | 1.99 | 1.66 | 0.34 |
| sem | 0.14 | 0.18 | 0.42 | 0.14 | 0.07 | 0.04 |
| % change | | −5 | −13 | −57 | −64 | −93 |
| p | | 0.375 | 0.240 | 0.001 | 0.001 | 0.001 |

The calculated IC50 value of Compound 1 for decreasing the DNA content of PAP2 cells is 2.77 µM.

The results in Tables 2a and 2b show that compounds of formula (I), in particular Compound 1, inhibit the growth of PAP2 cells in culture.

1.2. Colorimetric MTT assay

Cell number was estimated by the MTT assay performed essentially as described by T. Mosmann in J. Immunol Method 1983;65:55–63. Briefly, PAP2 cells were seeded at a concentration of $1 \times 10^4$ per dish in flat 96-well plates (Falcon) 5 h prior the addition of the tested drugs. Following an incubation period of 24 h, 48 h or 72 h, 10 µl of MTT [3-(4,5-dimethylthiazol-2-yl)-2,5-diphenyl tetrazolium bromide] dissolved in PBS at 5 mg/ml were added to each well and incubated at 37° C. for 4 h. The medium was then removed and 100 µl of 0.04N HCl in isopropanol were added to the wells. Absorbance of the converted dye was measured at 570 nm by a microplate reader with background substraction at 620 nm.

The calculated IC50 value of Compound 1 for the inhibition of the proliferation of PAP2 cells is 8.05 µM, as measured by the MTT method (after 72 h incubation). The results in Tables 3a, 3b and 3c confirm by another assay that compounds of formula (I), in particular Compound 1, inhibit the growth of PAP2 cells in culture.

Effect of Compound 1 on the Proliferation of PAP2 Cells Measured by the MTT assay

TABLE 3a

Incubation with Compound 1 for 24 h (OD at 570 nm)

| | \multicolumn{6}{c}{Compound 1 concentration} | | | | | |
|---|---|---|---|---|---|---|
| | 0 | 1.0 μM | 2.5 μM | 1.5 μM | 10 μM | 25 μM |
| OD | 39.9 | 39.5 | 37.6 | 35.9 | 28.9 | 21.4 |
| sem | 2.1 | 4.6 | 1.2 | 1.0 | 1.1 | 1.0 |
| % change | 0 | −1 | −6 | −10 | −28 | −46 |
| p | | 0.942 | 0.370 | 0.109 | 0.001 | 0.001 |

TABLE 3b

Incubation with Compound 1 for 48 h (OD at 570 nm)

| | Compound 1 concentration | | | | | |
|---|---|---|---|---|---|---|
| | 0 | 1.0 μM | 2.5 μM | 5 μM | 10 μM | 25 μM |
| Mean | 71.3 | 66.5 | 59.4 | 52.8 | 37.3 | 15.1 |
| sem | 5.2 | 4.9 | 2.5 | 3.1 | 1.9 | 0.7 |
| % change | 0 | −7 | −17 | −26 | −48 | −79 |
| p | | 0.516 | 0.059 | 0.009 | 0.001 | 0.001 |

TABLE 3c

Incubation with Compound 1 for 72 h (OD at 570 nm)

| | Compound 1 concentration | | | | | |
|---|---|---|---|---|---|---|
| | 0 | 1.0 μM | 2.5 μM | 5 μM | 10 μM | 25 μM |
| Mean | 366.0 | 336.8 | 334.4 | 287.4 | 136.6 | 29.0 |
| sem | 30.3 | 19.0 | 18.6 | 16.5 | 15.5 | 6.3 |
| % change | | −8 | −9 | −21 | −63 | −92 |
| p | | 0.427 | 0.388 | 0.039 | 0.001 | 0.001 |

3. Inhibition of DNA synthesis

DNA synthesis was measured by the incorporation of tritiated thymidine into trichloroacetic acid (TCA) precipitable material by cultured PAP2 cells. PAP2 cells were seeded in 24-well plates at $3 \times 10^4$ cells per well for 2 days. Then following preincubation with Compound 1 dissolved in ethanol, 0.5 μCi of methyl-[3H]-thymidine (specific activity 82 Ci/mmol) were added and labelling proceeded for 4 hours. The cells were then washed with 1 ml of cold phosphate-buffered saline (PBS), solubilized with 0.2 ml of 4% sodium dodecyl sulfate. The cellular extract was precipitated with 1 ml of 30% TCA, and kept for 1 h on ice. The precipitates were collected by filtration onto fiber glass filters and washed with 5 ml of 5% TCA. Radioactivity on the filters was counted in a liquid scintillation counter.

TABLE 4

Inhibition of DNA Synthesis by Compound 1 in ras Transfected Cells (PAP2) 3H-Thymidine incorporation into DNA (cpm)

| | Compound 1 concentration | | | | | |
|---|---|---|---|---|---|---|
| | 0 | 0.5 μM | 2 μM | 5 μM | 10 μM | 25 μM |
| cpm | 53021 | 45607 | 37130 | 30226 | 18772 | 14100 |
| sem | 7296 | 5354 | 2590 | 3945 | 1481 | 2766 |

TABLE 4-continued

Inhibition of DNA Synthesis by Compound 1 in ras Transfected Cells (PAP2) 3H-Thymidine incorporation into DNA (cpm)

| | Compound 1 concentration | | | | | |
|---|---|---|---|---|---|---|
| | 0 | 0.5 μM | 2 μM | 5 μM | 10 μM | 25 μM |
| % change | 0 | −14 | −30 | −43 | −65 | −73 |
| p | | 0.427 | 0.075 | 0.016 | 0.009 | 0.005 |

The calculated IC50 value of Compound 1 for the inhibition DNA synthesis in PAP2 cells is 3.75 μM.

Results in Table 4 show that compounds of formula (I), in particular Compound 1, inhibit DNA synthesis in ras transfected cells.

4. Induction of apoptosis

Compounds of formula (I) have also been shown to have a selective effect in stimulating cell death in the PAP2 cell line at 5 μM or higher concentrations. This specific effect in selectively stimulating programmed cell death in cancer cells was verified in two other human cancer cell lines (HepG2 and SW480) with Compound 1 indicating that these compounds not only inhibit cell growth but in addition produce cancer cell self-destruction (Table 5). This has been confirmed by gel electrophoresis showing DNA fragmentation, the hallmark of apoptosis.

TABLE 5

The Effect of Compound 1 on Cell Viability in Human Cancer Cell Lines

| Cell line | Nb of Viable Cells at 0 hrs | Nb of Viable Cells at 24 hrs | % Change |
|---|---|---|---|
| SW 480 | 38'800 | 0 | −100.0% |
| HepG2 | 214'700 | 82'000 | −61.8% |

Cells are cultured in 24-well plates for 48 h prior treatment.
Treatments are 10 μM compounds for 24 h.
Counting: cells are trypsinized and viable cells are counted.

5. Effect of Compound 1 on a wide range of human cancer cell lines

Compound 1 was tested for its anti-proliferative activity in a wide range of established human derived cancer cell lines to confirm the potential use of these compounds in relevant human cancers (Table 6). The results indicate that Compound 1 is effective in decreasing cell proliferation in greater than 90% of the more than 50 human cancer cell lines tested. Compounds of formula (I) therefore can be considered useful in treating a wide range of human cancers with and without ras-mutations.

TABLE 6

Anti-Proliferative Effects Compound 1 on Human Tumor Derived Cell Lines

| Tumor Type | Cell line | Inhibition of Proliferation (% Control) |
|---|---|---|
| Leukemia | CCRF-CEM | −61.8 |
| Leukemia | HL-60 (tb) | −95.3 |
| Leukemia | K-562 | −61.2 |
| Non-Small Cell Lung Cancer | A549/ATCC | −55.0 |
| Non-Small Cell Lung Cancer | EKVX | −27.0 |

TABLE 6-continued

Anti-Proliferative Effects Compound 1 on Human Tumor Derived Cell Lines

| Tumor Type | Cell line | Inhibition of Proliferation (% Control) |
|---|---|---|
| Non-Small Cell Lung Cancer | HOP-62 | −13.8 |
| Non-Small Cell Lung Cancer | HOP-92 | −85.1 |
| Non-Small Cell Lung Cancer | NCI-H23 | −21.8 |
| Non-Small Cell Lung Cancer | NCI-H322M | −12.5 |
| Non-Small Cell Lung Cancer | NCI-H460 | −40.7 |
| Non-Small Cell Lung Cancer | NCI-H522 | −59.8 |
| Colon Cancer | COLO 205 | −55.9 |
| Colon Cancer | HCC-2998 | −50.7 |
| Colon Cancer | HCT-116 | −68.7 |
| Colon Cancer | HCT-15 | −19.5 |
| Colon Cancer | HT29 | −83.0 |
| Colon Cancer | KM12 | −32.5 |
| Colon Cancer | SW-620 | −21.4 |
| CNS Cancer | SF-268 | −21.2 |
| CNS Cancer | SF-295 | −49.6 |
| CNS Cancer | SF-539 | +1.5 |
| CNS Cancer | SNB-19 | −55.8 |
| CNS Cancer | SNB-75 | −54.4 |
| CNS Cancer | U251 | −41.6 |
| Melanoma | LOX IMVI | −18.7 |
| Melanoma | MALME-3M | −20.4 |
| Melanoma | M14 | −66.7 |
| Melanoma | SK-MEL-2 | −6.1 |
| Melanoma | SK-MEL-28 | −25.0 |
| Melanoma | SK-MEL-5 | −51.8 |
| Melanoma | UACC-257 | −26.9 |
| Melanoma | UACC-62 | −30.9 |
| Ovarian Cancer | IGROV1 | −24.4 |
| Ovarian Cancer | OVCAR-3 | −47.3 |
| Ovarian Cancer | OVCAR-4 | −18.9 |
| Ovarian Cancer | OVCAR-5 | −17.6 |
| Ovarian Cancer | OVCAR-8 | −37.6 |
| Ovarian Cancer | SK-OV-3 | −28.1 |
| Renal Cancer | 786-0 | −28.7 |
| Renal Cancer | ACHN | −43.4 |
| Renal Cancer | CAKI-1 | −31.1 |
| Renal Cancer | SN12C | −1.0 |
| Renal Cancer | TK-10 | −18.6 |
| Renal Cancer | UO-31 | −35.9 |
| Prostate Cancer | PC-3 | −75.9 |
| Prostate Cancer | DU-145 | −21.3 |
| Breast Cancer | MCF-7 | −57.0 |
| Breast Cancer | MCF-7/ADR-RES | −49.3 |
| Breast Cancer | MDA-MB-231/ATCC | −50.9 |
| Breast Cancer | MDA-MB-435 | −51.6 |
| Breast Cancer | MDA-N | −43.3 |
| Breast Cancer | BT-549 | −51.3 |
| Breast Cancer | T-47D | −62.1 |

EXAMPLE 2

In vivo Results

INHIBITION OF TUMOUR GROWTH

Seven to nine-week old female nude mice (Swiss nu/nu) were injected s.c. with 0.5 ml of PAP2 cells ($5 \times 10^5$ cells per 0.5 ml of DMEM) on day 0. Oral treatment with Compound 1 (50 mg/kg) started on the same day. The treated group (n=1 8) received Compound I mixed with food (0.03% w/w) and the control group (n=22) received a diet without added compound. At day 15, the mice were weighed, sacrificed and the tumors were excised and weighed.

TABLE 7a

Effect of Oral Treatment with Compound 1 (50 mg/kg) on Tumor Weight Produced by s.c. Injection of PAP2 cells in Nude Mice

| Animal Group | Body Weight (g) (mean ± sem) | Tumor Weight (g) (mean ± sem) |
|---|---|---|
| Control n = 21) | 24.2 ± 0.5 | 0.228 ± 0.041 |
| Treated (n = 18) | 24.6 ± 0.7 | 0.053 ± 0.016 |
| % change | +2 | −77 |
| p | 0.6470 | 0.0006 |

The results in Table 7a show that the mean tumor weight in the treatment group decreased significantly, indicating that Compound 1 is a potent antitumor agent. Mice body weight in both control and treated groups are identical, thus establishing the lack of toxicity of Compound 1.

In another set of experiments Compound 1 was tested at doses of 12.5, 50 and 100 mg/kg. The results in Table 7b show that Compound 1 inhibits tumor growth in nude mice at doses as low as 12.5 mg/kg and in a dose dependent manner. These results demonstrate that compounds of formula (I), in particular Compound 1, are potent orally active antitumor compounds which do not have a toxic effect on normal cells, tissues or organs.

TABLE 7b

Decrease in Tumour Weight by Oral Treatment of Nude Mice Injected with PAP2 Cells with Different Doses of Compound 1

| Animal Group | Body Weight (g) (mean ± sem) | Tumor Weight (g) (mean ± sem) |
|---|---|---|
| Control (n = 14) | 24.7 ± 0.6 | 0.276 ± 0.056 |
| Treated, 12.5 mg/kg (n = 5) | 23.9 ± 0.8 | 0.053 ± 0.026 |
| % change | −3 | −81 |
| p | 0.4562 | 0.0472 |
| Treated, 50 mg/kg (n = 6) | 27.2 ± 1.0 | 0.037 ± 0.020 |
| % change | +10 | −87 |
| p | 0.0523 | 0.0211 |
| Treated, 100 mg/kg (n = 6) | 24.5 ± 0.3 | 0.025 ± 0.01[001b]1 |
| % change | −1 | −91 |
| p | 0.7619 | 0.0151 |

EXAMPLE A

Tetraisopropyl 2-(3,5-diisopropyl4-hydroxyphenyl)-ethenylidene-1,1-diphosphonate

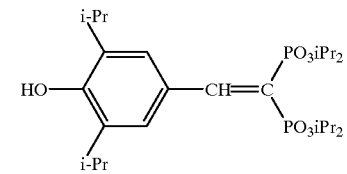

Titanium tetrachloride (13.83 g, 73 mmol) was added dropwise to dry THF (80 ml) maintained at 0° C. The resulting mixture was treated sequentially at 0° C. with 3,5-diisopropyl-4-hydroxybenzaldehyde (5.0 g, 24 mmol), tetraisopropyl methylenediphosphonate (10.85 g, 32 mmol) and N-methylmorpholine (14.71 g, 146 mmol). The reaction mixture was stirred for 12 h at room temperature and 80 ml water were added. The quenched reaction mixture was extracted with diethylether (3×60 ml), the combined ether fractions were extracted with a saturated NaCl solution until the aqueous washes had a neutral pH. After drying over MgSO$_4$, the organic solvent was evaporated and the residue was purified by column chromatography on silica using as eluant a mixture of CH$_2$Cl$_2$:MeOH (95:5) to give 8 g (62%) of a solid; mp=87–88° C.

MS: m/e=532: M$^+$, 367: M$^+$ —PO$_3$iPr$_2$
NMR (CDCl$_3$)
δ=8.22 (dd, J=31 and 48 Hz, 1H): Ph—CH=C—P$_2$
7.7 (s, 2H): aromatic H
5.6 (s, 1H): OH,
4.85-4.63 (2m, 4H): P—O—CHMe$_2$
3.16 (septet, 2H): Ph—CHMe$_2$
1.39, 1.36, 1.27, 1.23 and 1.16 (8d, 36H total): P—O—CHMe$_2$ and Ph—CHMe$_2$

EXAMPLE B
Tetraisopropyl 2-(3,5-diisopropyl-4-hydroxyphenyl)-ethylidene-1,1-diohosphonate

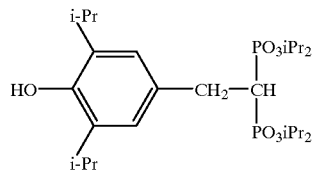

Tetraisopropyl 2-(3,5-diisopropyl-4-hydroxyphenyl)-ethenylidene-1,1-diphosphonate (5 g, 9.4 mmol) was dissolved in ethanol (50 ml) and the solution was hydrogenated for 4 h over 2 g of 10% palladium on carbon at 50 psi at room temperature. The catalyst was filtered, the solvent was evaporated and the residue was purified by column chromatography on silica using as eluant a mixture of CH$_2$Cl$_2$:MeOH (95:5) to give 2.5 g (50%) of a solid; mp=90–91° C.

MS: m/e =534: M$^+$, 369: M$^+$—PO$_3$iPr$_2$
NMR (CDCl$_3$)
δ=6.94 (m, 2H) : aromatic H,
4.8-4.7 (m, 5H): P—O—CHMe$_2$ and OH
3.2-3.1 (several m, 6H total ): Ph—CH$_2$—CH and Ph—CHMe$_2$
2.51 (tt, J=6 and 24H, 1H): Ph—CH$_2$—CH
1.33-1.21 (several d, 36H total): P—O—CHMe$_2$ and Ph—CHMe$_2$

EXAMPLE C
Tetraisopropyl 2-(3,4,5-trimethoxyphenyl)-ethenylidene-1,1-diphosphonate

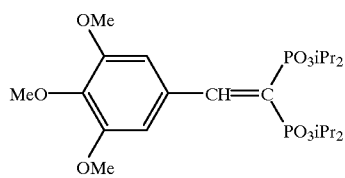

3,4,5-Trimethoxybenzaidehyde (7 g, 35.7 mmol) was treated with titanium tetrachloride, tetraisopropyl methylenediphosphonate and N-methylmorpholine in THF as described in Example A to give 11.5 g (62%) of the title compound.
MS: m/e=522: M$^+$, 357: M$^+$—PO$_3$iPr$_2$
NMR (CDCl$_3$)
δ=8.21 (dd, J=30 and 48 Hz, 1H): Ph—C H=C—P$_2$
7.28: (s, 2H): aromatic H 4.85-4.63 (2m, 4H): P—O—CHMe$_2$
3.9 (t, 9H): Ph—OMe
1.4, 1.36 and 1.22 (4d, 24H total): P—O—CHMe$_2$

EXAMPLE D
Tetraisopropyl 2-(3,4,5-trimethoxyphenyl)-ethylidene-1,1-diphosphonate

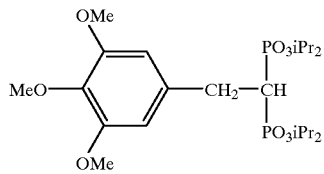

Tetraisopropyl 2-(3,4,5-trimethoxyphenyl)-ethenylidene-1,1-diphosphonate (7 g, 13.4 mmol) was hydrogenated over 10% Pd/C as described in Example B to give 5.7 g (81%) of the title compound.

MS: m/e=524: M$^+$, 359: M$^+$—PO$_3$iPr$_2$
NMR (CDCl$_3$)
δ=6.55 (s, 2H): aromatic H,
4.8-4.7 (m, 4H): P—O—CHMe$_2$
3.85 and 3.81 (2s, 9H): Ph—OMe
3.17 (dt, J=6 and 16 Hz, 2H): Ph—CH$_2$—CH
2.50 (tt, J=6 and 24 Hz, 1H): Ph—CH$_2$—CH
1.33-1.26 (several d, 24H total): P—O—CHMe$_2$

EXAMPLE E
Tetraisopropyl 2-(3-tert-butyl-4-hydroxy-5-methylphenyl)-ethenylidene-1,1-diphosphonate

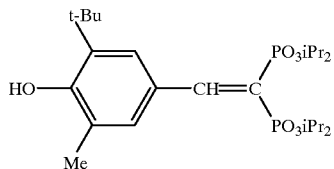

3-Tert-butyl-4-hydroxy-5-methylbenzaldehyde (6 g, 31.3 mmol) was treated with titanium tetrachloride, tetraisopropyl methylenediphosphonate and N-methylmorpholine in THF as described in Example A to give 4.2 g (62%) of the title compound.

MS: m/e=518: M$^+$, 353: M$^+$—PO$_3$iPr$_2$
NMR (CDCl$_3$)
δ=8.19 (dd, J=30 and 48 Hz, 1H): Ph—CH=C—P$_2$
7.71-7.67 (m, 2H) aromatic H,
5.6 (s, 1H): OH,
4.8-4.7 (2m, 4H): P—O—CHMe$_2$
2.26 (s, 3H): Ph—Me
1.40 (s, 9H): Ph—t—Bu
1.38, 1.36, 1.24 and 1.20 (8d, 24H total): P—O—CHMe$_2$

EXAMPLE F
Tetraisopropyl 2-(3-tert-butyl-4-hydroxy-5-methylphenyl)-ethylidene-1,1-diphosphonate

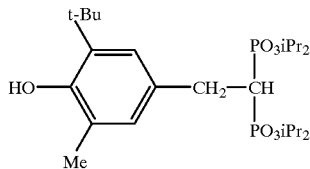

Tetraisopropyl 2-(3-tert-butyl-4-hydroxy-5-methylphenyl)-ethenylidene-1,1-diphosphonate (5 g, 9.6 mmol) was hydrogenated over 10% Pd/C as described in Example B to give 2.9 g (58%) of the title compound.
MS: m/e=520: $M^+$, 355: $M^+$—$PO_3iPr2$
NMR ($CDCl_3$)
δ=7.02 and 6.92 (2m, 2H): aromatic H,
4.8–4.7 (m, 5H): P—O—$CHMe_2$ and OH
3.11 (dt, J=6 and 17 Hz, 2H): Ph—$CH_2$—CH
2.49 (tt, J=6 and 24 Hz, 1H): Ph—$CH_2$—CH
2.21 (s, 3H): Ph—Me
1.39 (s, 9H): Ph—t—Bu
1.31, 1.26 and 1.24 ( 3d, 24H): P—O—$CHMe_2$

EXAMPLE G
Tetraisopropyl 2-(3-ethoxy-4-hydroxyphenyl)-ethenylidene-1,1-diphosphonate

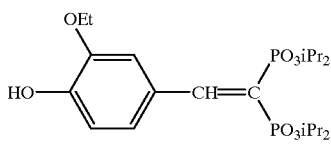

3-Ethoxy-4-hydroxybenzaldehyde (6 g, 36.1 mmol) was treated with titanium tetrachloride, tetraisopropyl methylenediphosphonate and N-methylmorpholine in THF as described in Example A to give 4.2 g (62%) of the title compound, mp=143–144° C.
MS: m/e=492: $M^+$, 327: $M^+$—$PO_3iPr_2$
NMR ($CDCl_3$)
δ=8.19(dd, J=31 and 48 Hz, 1H): Ph—CH=C—$P_2$
7.9, 7.3 and 6.91(3m, 3H): aromatic H,
6.2 (s, 1H) : OH
4.85-4.63 (2m, 4H): P—O—$CHMe_2$
4.19 (q, J=7 Hz): Ph—$OCH_2$—$CH_3$
1.46 (t, J=7 Hz): Ph—$OCH_2$—$CH_3$
1.39, 1.36, 1.23 and 1.21 (4d, 24H total): Ph—$CHMe_2$

EXAMPLE H
Tetraisoproyl 2-(3-ethoxy-4-hydroxy-phenyl)-ethylidene-1,1-diphosphonate

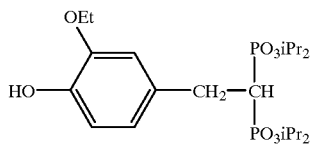

Tetraisopropyl 2-(3-ethoxy-4-hydroxyphenyl)-ethenylidene-1,1-diphosphonate (5 g, 10.16 mmol) was hydrogenated over 10% Pd/C as described in Example B to give 4.5 g (90%) of the title compound.
MS: m/e=494: $M^+$, 329: $M^+$—$PO_3iPr_2$
NMR ($CDCl_3$)
δ=6.85-6.75 (several m, 3H): aromatic H
5.65 (s, 1H): OH
4.8-4.7 (m, 4H): P—O—$CHMe_2$
4.10 (q, J=7 Hz): Ph—$OCH_2$—$CH_3$
3.14 (dt, J=6 and 16 Hz, 2H): Ph—$CH_2$—CH
2.45 (tt, J=6 and 24 Hz, 1H): Ph—$CH_2$—CH
1.43 (t, J=7 Hz): Ph—$OCH_2$—$CH_3$
1.32-1.25 (4 partially overlapping d, 24H total): P—O—$CHMe_2$

EXAMPLE I
Tetraethyl 2-(3,5-di-tert-butyl-4-methoxyphenyl)-ethenylidene-1,1-diphosphonate

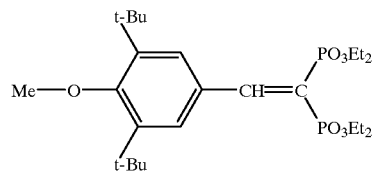

3,5-Di-tert-butyl-4-methoxybenzaldehyde (2.0 g, 8.1 mmol) was treated with titanium tetrachloride, tetraethyl methylenediphosphonate and N-methylmorpholine in THF as described in Example A to give 3.0 g (72%) of the title compound, mp=66–67° C.
MS: m/e=518: $M^+$, 381: $M^+$—$PO_3Et_2$
NMR ($CDCl_3$)
δ=8.26 (dd, J=30 and 48 Hz, 1H): Ph—CH=C—$P_2$
7.8 (s, 2H): aromatic H,
4.25-4.00 (2m, 8H): P—O—$CH_2$—$CH_3$
3.69 (s, 3H): Ph—OMe
1.44 (s, 18H): Ph—t—Bu
1.38 and 1.70 (2t, 12H): Ph—$OCH_2$—$CH_3$

EXAMPLE J
Tetraisopropyl 1-(3,5-di-tert-butyl-4-hydroxyphenyl)-butylidene-2,2-diphosphonate

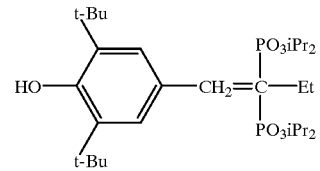

Tetraisopropyl propylidene-1,1-diphosphonate was prepared by reacting tetraisopropyl methylenediphosphonate with 3 equivalents of ethyl iodide in presence of NaH in THF.
Tetraisopropyl propylidene-1,1-diphosphonate (2.2 g, 6.0 mmol) was added to a suspension of 60% NaH (0.5 g, 12.0 mmol) in 20 ml of dry THF and the mixture was stirred until the NaH disappeared. 3,5-di-tert-butyl-4-hydroxybenzylchloride (1.5 g, 6 mmol) in 10 ml THF was added and the mixture was refluxed overnight. After work up, column chromatography on silica using $CHCl_3$: AcOEt (8:2) as eluant gave 1.5 g (42%) of the title compound.
MS: m/e=590: $M^+$, 425: $M^+$—$PO_3{}^iPr_2$, base Peak 341: $M^+$-2× propen
mp=131–132° C.

EXAMPLE K

Typical Example of Compound Formulation
Active Component
  Compound 1
Inactive Component
  Pregelatinazed Starch NF
  Size 3 opaque dark blue gelatin capsules Representative Batch Formula
Typical batch size 2000 capsules

| Ingredients | g/batch | | |
|---|---|---|---|
| | 1 mg | 10 mg | 50 mg |
| Compound 1 | 2.00 | 20.0 | 100.0 |
| Pregelatinized starch NF | 431.6 | 408.8 | 291.0 |
| Total | 433.6 | 428.8 | 391.0 |

What is claimed is:

1. A method of treating or preventing a neoplastic disease in a patient, wherein the neoplastic disease is chosen from cancers of the hemopoietic and immune system and cancers of the pancreas, colon, breast, thyroid, brain, lung, head and neck, said method comprising administering to a patient in need of such therapy, a therapeutically effective amount of a compound represented by formula I

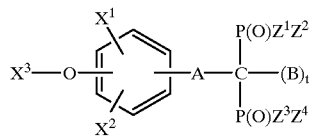

wherein:
  $Z^1$, $Z^2$, $Z^3$ and $Z^4$ are each —OR wherein R is independently chosen from —H and straight or branched alkyl comprising from 1 to 8 carbon atoms;
  $X^1$ and $X^2$ are independently straight or branched alkyl comprising from 1 to 8 carbon atoms;
  $X^3$ is —H;
  A is —$(CH_2)_n$—, wherein n is an integer from 1 to 7;
  B is chosen from —H and alkyl comprising from 1 to 4 carbon atoms; and
  t is 1;
  or a pharmaceutically acceptable salt thereof.

2. The method according to claim 1, wherein $Z^1$, $Z^2$, $Z^3$ and $Z^4$ are each independently chosen from hydroxy, methoxy, ethoxy, n-propyloxy, isopropyloxy, n-butyloxy, sec-butyloxy, and tert-butyloxy.

3. The method according to claim 2, wherein $Z^1$, $Z^2$, $Z^3$ and $Z^4$ are the same.

4. The method according to claim 3, wherein $Z^1$, $Z^2$, $Z^3$ and $Z^4$ are each isopropyloxy.

5. The method according to claim 1, wherein $X^1$ and $X^2$ are independently straight or branched alkyl comprising from 1 to 5 carbon atoms.

6. The method according to claim 5, wherein $X^1$ and $X^2$ are independently chosen from methyl, ethyl, n-propyl, isopropyl, s-butyl and t-butyl.

7. The method according to claim 6, wherein $X^1$ and $X^2$ are the same.

8. The method according to claim 7, wherein $X^1$ and $X^2$ are each t-butyl.

9. The method according to claim 1, wherein the compound is tetraisopropyl 2-(3,5-di-tert-butyl-4-hydroxyphenyl)-ethylidene-1,1-diphosphonate.

10. The method according to claim 1, wherein the compound is chosen from:
  2-(3,5-di-tert-butyl-4-hydroxyphenyl)-ethylidene-1,1-diphosphonic acid;
  tetramethyl 2-(3,5-di-tert-butyl-4-hydroxyphenyl)-ethylidene-1,1-diphosphonate;
  tetraethyl 2-(3,5-di-tert-butyl-4-hydroxyphenyl)-ethylidene-1,1-diphosphonate;
  tetra-n-propyl 2-(3,5-di-tert-butyl-4-hydroxyphenyl)-ethylidene-1,1-diphosphonate;
  tetra-n-butyl 2-(3,5-di-tert-butyl-4-hydroxyphenyl)-ethylidene-1,1-diphosphonate;
  tetraisopropyl 2-(3,5-di-sec-butyl-4-hydroxyphenyl)-ethylidene-1,1-diphosphonate;
  tetraethyl 2-(3,5 -diisopropyl-4-hydroxyphenyl)-ethylidene-1,1-diphosphonate;
  tetraisopropyl 2-(3,5-diisopropyl-4-hydroxyphenyl)-ethylidene-1,1-diphosphonate;
  tetraethyl 2-(3-tert-butyl-4-hydroxy-5-methylphenyl)-ethylidene-1,1-diphosphonate;
  tetraisopropyl 2-(3-tert-butyl-4-hydroxy-5-methylphenyl)-ethylidene-1,1-diphosphonate;
  tetraethyl 1-(3,5-di-tert-butyl-4-hydroxyphenyl)-butylidene-2,2-diphosphonate; and
  tetraisopropyl 1-(3,5-di-tert-butyl-4-hydroxyphenyl)-butylidene-2,2-diphosphonate.

11. The method according to claim 1 wherein the neoplastic disease is a ras dependent cancer.

12. The method according to claim 1 wherein the neoplastic disease is chosen from lymphomas and leukemias.

13. A method of preventing transformation of a normal cell of a patient into a tumor cell by mutated ras activities, wherein said tumor cell is chosen from cancers of the hemopoietic and immune system and cancers of the pancreas, colon, breast, thyroid, brain, lung, head and neck, said method comprising treating a normal cell of a patient in need of such treatment, with an amount of a compound effective to block said mutated ras activities, said compound represented by formula I

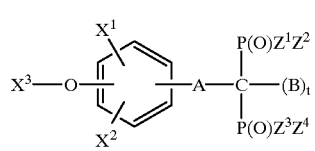

wherein:
  $Z^1$, $Z^2$, $Z^3$ and $Z^4$ are each —OR wherein R is independently chosen from —H and straight or branched alkyl comprising from 1 to 8 carbon atoms;
  $X^1$ and $X^2$ are independently straight or branched alkyl comprising from 1 to 8 carbon atoms;
  $X^3$ is —H;
  A is —$(CH_2)_n$—, wherein n is an integer from 1 to 7;
  B is chosen from —H and alkyl comprising from 1 to 4 carbon atoms; and
  t is 1;
  or a pharmaceutically acceptable salt thereof.

14. The method according to claim 13, wherein the compound is tetraisopropyl 2-(3,5-di-tert-butyl-4-hydroxyphenyl)-ethylidene-1,1-diphosphonate.

15. A method of treating or preventing a neoplastic disease in a patient, wherein the neoplastic disease is chosen from leukemia, non-small cell lung cancer, colon cancer, CNS cancer, melanoma, ovarian cancer, renal cancer, prostrate cancer and breast cancer, said method comprising administering to a patient in need of such therapy, a therapeutically effective amount of a compound represented by formula I

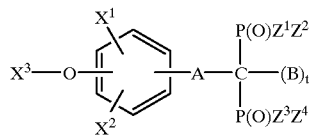

wherein:
- $Z^1$, $Z^2$, $Z^3$ and $Z^4$ are each —OR wherein R is independently chosen from —H and straight or branched alkyl comprising from 1 to 8 carbon atoms;
- $X^1$ and $X^2$ are independently straight or branched alkyl comprising from 1 to 8 carbon atoms;
- $X^3$ is —H;
- A is —$(CH_2)_n$—, wherein n is an integer from 1 to 7;
- B is chosen from —H and alkyl comprising from 1 to 4 carbon atoms; and
- t is 1;

or a pharmaceutically acceptable salt thereof.

16. A method of treating or preventing a neoplastic disease in a patient, wherein the neoplastic disease is chosen from cancers of the kidney and liver, said method comprising administering to a patient in need of such therapy, a therapeutically effective amount of a compound represented by formula I

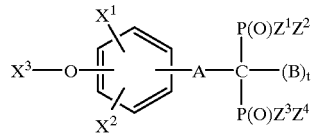

wherein:
- $Z^1$, $Z^2$, $Z^3$ and $Z^4$ are each —OR wherein R is independently chosen from —H and straight or branched alkyl comprising from 1 to 8 carbon atoms;
- $X^1$ and $X^2$ are independently straight or branched alkyl comprising from 1 to 8 carbon atoms;
- $X^3$ is —H;
- A is —$(CH_2)_n$—, wherein n is an integer from 1 to 7;
- B is chosen from —H and alkyl comprising from 1 to 4 carbon atoms; and
- t is 1;

or a pharmaceutically acceptable salt thereof.

* * * * *